(12) United States Patent
Sekine et al.

(10) Patent No.: US 8,715,984 B2
(45) Date of Patent: *May 6, 2014

(54) MODIFIED TRNA CONTAINING UNNATURAL BASE AND USE THEREOF

(75) Inventors: Shun-ichi Sekine, Tokyo (JP); Ryuya Fukunaga, Tokyo (JP); Shigeyuki Yokoyama, Kanagawa (JP); Ichiro Hirao, Kanagawa (JP); Yoko Harada, Kanagawa (JP)

(73) Assignee: Riken, Saitama (JP)

( * ) Notice: Subject to any disclaimer, the term of this patent is extended or adjusted under 35 U.S.C. 154(b) by 134 days.

This patent is subject to a terminal disclaimer.

(21) Appl. No.: 12/866,720

(22) PCT Filed: Feb. 3, 2009

(86) PCT No.: PCT/JP2009/051808
§ 371 (c)(1),
(2), (4) Date: Aug. 27, 2010

(87) PCT Pub. No.: WO2009/099073
PCT Pub. Date: Aug. 13, 2009

(65) Prior Publication Data
US 2010/0323364 A1 Dec. 23, 2010

(30) Foreign Application Priority Data
Feb. 7, 2008 (JP) ................................. 2008-027567

(51) Int. Cl.
*C12N 9/00* (2006.01)
*C12P 21/06* (2006.01)

(52) U.S. Cl.
USPC .......................... 435/183; 435/68.1; 435/69.1

(58) Field of Classification Search
None
See application file for complete search history.

(56) References Cited

U.S. PATENT DOCUMENTS

| | | | |
|---|---|---|---|
| 7,101,992 B1 | 9/2006 | Hirao et al. | |
| 2005/0136513 A1 | 6/2005 | Zhang et al. | |
| 2007/0111193 A1 | 5/2007 | Zhang et al. | |
| 2010/0285598 A1* | 11/2010 | Hirao et al. ...................... | 436/94 |
| 2011/0124080 A1 | 5/2011 | Zhang et al. | |
| 2012/0282626 A1 | 11/2012 | Zhang et al. | |

FOREIGN PATENT DOCUMENTS

| | | |
|---|---|---|
| JP | 2006180701 A | 7/2006 |
| JP | 3893057 B2 | 3/2007 |
| JP | 2007061087 A | 3/2007 |
| JP | 2007-514447 A | 6/2007 |
| WO | WO-2004/039989 A1 | 5/2004 |
| WO | WO-2007066737 A1 | 6/2007 |

OTHER PUBLICATIONS

Tzvetkova et al. Biomimetic Aminoacylation of Ribonucleotides and RNA with Aminoacyl Phosphate Esters and Lanthanum Salts. Journal of the American Chemical Society, vol. 129, pp. 15848-15854.*
Phelps et al. Modified Nucleotides in tRNALys and tRNAVal are Important for Translocation. 2004. J. Mol. Biol. vol. 338, pp. 439-444.*
Mitsui et al. An Unnatural Hydrophobic Base Pair with Shape Complementarity between Pyrrole-2-carbaldehyde and 9-Methylimidazo [(4,5)-b]pyridine. 2003. JACS. vol. 125, pp. 5298-5307.*
Capone et al. Amber, ochre and opal suppressor tRNA genes derived from a human serine tRNA gene. The EMBO Journal. vol. 4, No. 1, pp. 213-221.*
SEQ ID No. 2 Sequence Alignment. May 7, 2013. 4 pages.*
Mitsui, T., et al., "An Efficient Unnatural Base Pair for a Base-Pair-Expanded Transcription System," J. Am. Chem. Soc., vol. 127, pp. 8652-8658 (2005).
Ohtsuki, T., et al., "Unnatural base pairs for specific transcription," PNAS, vol. 98, No. 9, pp. 4922-4925 (2001).
Kiga, D., et al., "An engineered *Escherichia coli* tyrosyl-tRNA synthetase for site-specific incorporation of an unnatural amino acid into proteins in eukaryotic translation and its application in a wheat germ cell-free system," PNAS, vol. 99, No. 15, pp. 9715-9720 (2002).
Ohno, S., et al., "Changing the Amino Acid Specificity of Yeast Tyrosyl-tRNA Synthetase by Genetic Engineering," J. Biochem, vol. 130, No. 3, pp. 417-423 (2001).
Fukunaga, R., et al., "Structural insights into the Second Step of RNA-dependent Cysteine Biosynthesis in Archaea: Crystal Structure of Sep-tRNA:Cys-tRNA Synthase from *Archaeoglobus fulgidus*," J. Mol. Biol., vol. 370, pp. 128-141 (2007).
Breitschopf, K. et al., "The discriminator bases G73 in human tRNA$^{Ser}$ and A73 in tRNA$^{Leu}$ have significantly different roles in the recognition of aminoacyl-tRNA synthetases," Nucleic Acids Res., vol. 24, No. 3, pp. 405-410 (1996).
Fukunaga, R., et al., "Phosphoserine aminoacylation of tRNA bearing an unnatural base anticodon," Biochem. Biophy. Res. Comm., vol. 372, pp. 480-485 (2008).
Fukunaga, R., et al., "Structural insights into the first step of RNA-dependent cysteine biosynthesis in archaea," Nature Struc. Molec. Bio., vol. 14, No. 4, pp. 272-279 (2007).
Grosjean, H., et al., "Enzymatic Formation of Modified Nucleosides in tRNA: Dependence on tRNA Architecture," J. Mol. Biol., vol. 255, pp. 67-85 (1996).
Hirao, I., et al., "An unnatural base pair for incorporating amino acid analogs into proteins," Nat. Biotech., vol. 20, No. 2, pp. 177-182 (2002).

(Continued)

*Primary Examiner* — Anne Gussow
*Assistant Examiner* — Channing S Mahatan
(74) *Attorney, Agent, or Firm* — Birch, Stewart, Kolasch & Birch, LLP

(57) ABSTRACT

In the method for introducing a noncanonical amino acid residue into a desired position in a protein, the structure of tRNA is so modified as to have improved affinity for aminoacyl-tRNA synthetase or improved specificity to aminoacyl-tRNA synthetase. An unnatural base is contained at any position in tRNA, whereby the efficiency of aminoacylation of the tRNA with a noncanonical amino acid can be improved.

7 Claims, 4 Drawing Sheets

(56) References Cited

OTHER PUBLICATIONS

Hirao, I., et al., "An unnatural hydrophobic base pair system: site-specific incorporation of nucleotide analogs into DNA and RNA," Nat. Meth., vol. 3, No. 9, pp. 729-735 (2006).

Hirao, I., et al., "Unnatural base pair systems for DNA/RNA-based biotechnology," Curr. Opin. Chem. Biol., vol. 10, pp. 622-627 (2006).

Kimoto, M., et al., "Fluorescent probing for RNA molecules by an unnatural base-pair system," Nucl. Acids Res., vol. 35, No. 16, pp. 5360-5369 (2007).

Martin, F., et al., "Single amino acid changes in AspRS reveal alternative routes for expanding its tRNA repertoire in vivo," Nucl. Acids Res., vol. 32, No. 13, pp. 4081-4089 (2004).

Perret, V., et al., "Relaxation of a transfer RNA specificity by removal of modified nucleotides," Nature, vol. 344, pp. 787-789 (1990).

Senger, B., et al., "The Modified Wobble Base Inosine in Yeast tRNA$^{Ile}$ is a Positive Determinant for Aminoacylation by Isoleucyl-tRNA Synthetase," Biochem., vol. 36, pp. 8269-8275 (1997).

Sylvers, L. A., et al., "A 2-Thiouridine Derivative in tRNA$^{Glu}$ is a Positive Determinant for Aminoacylation by *Escherichia coli* Glutamyl-tRNA Synthetase," Biochem., vol. 32, pp. 3836-3841 (1993).

Hirao et al., "A Two-Unnatural-Base-Pair System toward the Expansion of the Genetic Code," Journal of the American Chemical Society, ACS Publications, vol. 126, No. 41, Oct. 20, 2004, pp. 13298-13305.

Office Action issued by the European Patent Office for Application No. 09709377.7 on Aug. 14, 2013, 10 pages.

Wang et al., "Expanding the Genetic Code of *Escherichia coli*," Science, American Association for the Advancement of Science, vol. 292, Apr. 20, 2001, pp. 498-500.

Hirao, "Expansion of the genetic code by the creation of unnatural base pairs", Saitama Kougyou University, 2003, pp. 16-20, not in English.

Japanese Office Action dated Dec. 3, 2013 for Application No. 2009-552478 9 pages. English translation.

Yokoyama, "Jinkouteki na iden/saibou jouhou shori system wo mezashite" Yokoyama jouhou bunshi Project (Oct. 1996-Sep. 2001) kenkyuu shuuryou houkokusho, 2002, vol. 1 (main), pp. 213-222, not in English.

* cited by examiner

US 8,715,984 B2

MODIFIED TRNA CONTAINING UNNATURAL BASE AND USE THEREOF

The present application is a National Stage filing under 35 U.S.C. §371 of PCT International Application No. PCT/JP2009/051808 filed on Feb. 3, 2009, which claims priority of Japanese patent application No. 2008-027567, filed on Feb. 7, 2008 under 35 U.S.C. §119 (a)-(d), the disclosure of which is incorporated herein in its entirety by reference thereto.

TECHNICAL FIELD

The present invention is related to a modified tRNA containing an unnatural base and the use thereof, and in more detail, a combination of the modified tRNA having the unnatural base at a specific site with an aminoacyl-tRNA synthetase which can activate this modified tRNA, and a method for efficiently introducing a noncanonical amino acid into a desired position in a protein using such a combination.

BACKGROUND

A/T and G/C within double-stranded natural DNA form "exclusive" base pairs, respectively, via specific hydrogen bonds, respectively. However, the fact that natural nucleic acid has 4 kinds of bases (2 kinds of base pairs) provides a limitation to the chemical and physical variety of nucleic acid. If the genetic codes can be extended due to unnatural base pairs (artificial base pairs), it is beneficial to introduce various functional elements into desired positions into nucleic acids or proteins. So far, in the research of the unnatural base pairs, searches have been directed to those which could be antagonistic to natural base pairs in each process of replication, transcription and translation based on the combination utilizing the hydrogen bonds between the bases or the combination utilizing the hydrophobicity of the bases.

Inventors of the present invention have developed various kinds of unnatural base pairs which have a different hydrogen bond type compared to natural base pairs and can exclude a pairing with a natural base due to the steric hindrance. For example, 2-amino-6-dimethylaminopurine (x) and 2-amino-6-thienylpurine (s) introducing a bulky substituted group at position 6 of purine and pyridine-2-on (y) having a hydrogen atom at a site complementary to the bulky substituted group have been designed. When they have investigated an incorporation into DNA by Klenow fragment and an incorporation into RNA by T7 RNA polymerase regarding these x-y and s-y base pairs formation, the unnatural base pair s-y utilizing the steric hindrance showed an extremely high selectivity for transcription reaction, and a RNA, in which y is site-specifically incorporated at a site complementary to s within a template DNA, was able to be synthesized (for example, see Patent Document 1). And then, the genetic code was extended using this s-y base pair to create a new codon-anticodon pairs corresponding to the noncanonical amino acid, thereby they have succeeded in synthesizing a protein incorporating the noncanonical amino acid site-specifically in vitro (for example, see Non-Patent Document 1). However, its selectivity between unnatural base pairs in replication reaction has not been so high compared to that in transcription reaction.

Recently, inventors of the present invention have developed an unnatural base pair, 7-(2-thienyl)-imidazo[4,5-b]pyridine (Ds) and pyrrole-2-carboaldehyde (Pa), having high selectivity and incorporation efficiency for replication and transcription reactions based on the formation of base pairs due to hydrophobic interactions (for example, see Non-Patent Document 2). In the replication reaction, a self-pairing of Ds bases is suppressed by using γ-amidotriphosphate to form a selective base pair between Ds and Pa. On the other hand, in the transcription reaction, it is possible to synthesize RNA by standard T7 RNA polymerase reaction based on complementary property of the Ds-Pa base pair.

However, the conventional technique relating to these unnatural bases has been studied about a recognition of unnatural bases by DNA polymerase or RNA polymerase and also about a specific complementary property and a stability between unnatural base pairs, whereas studies about various factors to act on in a translation stage, for example, an influence onto interaction between tRNA and aminoacyl-tRNA synthetase have not been studied yet.

On the other hand, the genetic codes can be extended by assigning the noncanonical amino acid to nonsense codons that are UAA (ochre), UGA (opal) or UAG (amber). The suppressor tRNA (tRNA$^{ochre}$, tRNA$^{opal}$, and tRNA$^{amber}$) corresponding to these nonsense codons have nonsense anticodons, UUA, UCA and CUA, respectively, and they are used with a mutant aminoacyl-tRNA synthetase which can attach the noncanonical amino acid to these suppressor tRNA for an extension of the genetic codes.

For example, the phosphorylation at a side chain of serine in a protein is a post-translational modification, relating to many important biological phenomena such as signal transduction and the like. If phosphoserine can be introduced into a desired position in a protein by extending genetic codes, it will be a very important tool for study of a role of the phosphorylation at a serine residue of a protein. Phosphoseryl-tRNA synthetase (SepRS) is a noncanonical aaRS, which recognizes phosphoserine in several archaebacterium and ligates it to tRNA$^{Cys}$ with anticodon GCA. Inventors of the present invention have already analyzed the three-dimensional structure of SepRS/tRNA$^{Cys}$/phosphoserine complex derived from *Archaeroglobus fulgidus*. And then, based on the structure of the complex, the SepRS was modified to recognize a mutant tRNA$^{Cys}$ having UCA and CUA at anticodon, thereby it was shown that phosphoserine can be introduced into nonsense codon using such a mutant SepRS/tRNA pair (for example, see Non-Patent Document 3).

[Patent Document 1] Japanese Patent No. 3893057
[Non-Patent Document 1] Hirao, I. et al., An unnatural pair for incorporating amino acid analogs into proteins, Nature Biotechnology, Vol. 20, pp. 177-182 (2002)
[Non-Patent Document 2] Hirao, I. et al., An unnatural hydrophobic base pair system: site-specific incorporation of nucleotide analogs into DNA and RNA, Nature Methods, Vol. 3, pp. 729-735 (2006)
[Non-Patent Document 3] Fukunaga, R. & Yokoyama, S., Structural insights into the first step of RNA-dependent cysteine biosynthesis in archaea, Nature Structural & Molecular Biology, Vol. 14, pp. 272-279, (2007)

SUMMARY

The entire disclosures of the above Patent Document 1 and Non-Patent Documents 1-3 are incorporated herein by reference thereto. In the following, an analysis of related technique by this invention will be given.

In the method of introducing noncanonical amino acids using nonsense codons, in the case where translation terminator recognizes a nonsense codon within a protein coding region, the translation reaction is terminated at its recognition site and a truncated form of the protein is produced. Further, the noncanonical amino acid is introduced not only into a targeted nonsense codon within a target gene but also into natural stop codons of non-target genes, thereby a readthrough of these proteins occurs. As a result, there is a problem that the efficiency of the protein synthesis incorporating the targeted noncanonical amino acid falls.

In addition, the aminoacyl-tRNA synthetase recognizes a specific nucleotide of the cognate tRNA, and distinguishes it from other tRNA. Hence, it could be that the efficiency of synthesis (recognition) of the suppressor tRNA by the targeted aminoacyl-tRNA synthetase falls because the aminoacyl-tRNA synthetase recognizing the anticodon of cognate tRNA cannot recognize the anticodon corresponding to the nonsense codon. In such a case, it is beneficial that not only the aminoacyl-tRNA synthetase structure is modified but also an affinity with and a specificity for the aminoacyl-tRNA synthetase can be improved by modifying the structure of tRNA at a position interacting with the above modified aminoacyl-tRNA synthetase.

The present invention was made to solve the above problem, and the present invention provides a method that an unnatural base is site-specifically introduced at a specific site of tRNA, and that a noncanonical amino acid is efficiently attached to a modified tRNA containing an unnatural base, and a method that a protein containing the noncanonical amino acid at a desired position is synthesized (site-)specifically and efficiently using a combination of such a modified tRNA with the aminoacyl-tRNA synthetase.

That is, according to a first aspect of the present invention, a modified tRNA of the present invention is characterized by a modified tRNA for introducing a noncanonical amino acid into a desired position(s) in a protein; wherein the modified tRNA comprises unnatural bases at any position(s) of said tRNA, thereby improving efficiency of aminoacylation reaction thereof with the noncanonical amino acid. It is preferred that said aminoacylation reaction is catalyzed by a mutant aminoacyl-tRNA synthetase. It is also preferred that the unnatural base is comprised at any position(s) other than conserved residues of tRNA. In a more preferred mode, the unnatural base is at a position(s) interacting with the aminoacyl-tRNA synthetase, and included in at least one position selected from the class consisting of first three base pairs of accepter stem, anticodon, discriminator, whole extra arm in the case of type II tRNA, position 20, position 32, position 37 and position 38.

According to other aspect of the present invention, there is provided a method of screening a modified tRNA for improving aminoacylation reaction of tRNA by a noncanonical amino acid. The method comprises:
(a) preparing a suppressor tRNA recognized by an aminoacyl-tRNA synthetase which can activate the noncanonical amino acid;
(b) synthesizing the modified tRNA introducing an unnatural base at any position(s) of said tRNA;
(c) measuring an aminoacylation activity of the modified tRNA under existence of standard and noncanonical amino acids, and the aminoacyl-tRNA synthetase for these amino acids; and
(d) selecting the modified tRNA, in which an incorporating amount of the noncanonical amino acid is increased or an incorporating rate of the noncanonical amino acid is improved compared to that of the standard amino acid. It is preferred that a tRNA gene including the unnatural base is prepared and the transcription reaction is performed with said tRNA gene as a template DNA in the synthesis of the modified tRNA in the above step (b). It is also preferred that said tRNA gene is capable of being amplified by polymerase chain reaction.

According to a still other aspect of the present invention, there is provided a production method of a protein incorporating a noncanonical amino acid characterized in that the following (a) (b) and (c) are expressed in a cell or in a cell extract solution under existence of unnatural bases and noncanonical amino acids:
(a) an aminoacyl-tRNA synthetase which can activate the noncanonical amino acid;
(b) a modified tRNA of the present invention recognized by said aminoacyl-tRNA synthetase; and
(c) a mRNA coding a desired protein having a nonsense codon or a codon including an unnatural base at a desired position(s). In a preferred mode, as the noncanonical amino acid, phosphoserine, pyrolysine, lysine derivative or tyrosine derivative and the like are listed.

According to the present invention, it is possible to synthesize a new combination of the modified tRNA introducing the unnatural base into a specific position(s) in tRNA with the mutant aminoacyl-tRNA synthetase, which specifically recognizes the modified tRNA and also can activate the noncanonical amino acid. As for the combination, it is possible to provide a combination that not only a production yield of the aminoacyl-tRNA with the noncanonical amino acid is increased but also specificity to the noncanonical amino acid is high. That is, it is beneficial for a synthesis of a protein incorporating the noncanonical amino acid with high specificity by suppressing a background caused by unwanted incorporation of standard amino acid.

In addition, according to the method of the present invention, it is possible to synthesize a new combination which is specific to respective of various different kinds of the noncanonical amino acids. Thereby, it is also easy to produce a protein introducing a plurality of (or several) kinds of noncanonical amino acids into various positions, then a protein having new function(s) which can not be produced in the conventional method is synthesized, and these can be prepared with ease.

PREFERRED MODES

In the present invention, the terms "unnatural" is used in a context explaining an nucleobase and it means any base other than natural adenine (A), guanine (G), cytosine (C), tymine (T), urasil (U) and modified bases existing in natural tRNA. The term "noncanonical" is used in a context explaining amino acids and the "noncanonical amino acid(s)" means amino acid(s) other than 20 kinds of standard amino acids defined in the genetic code dictionary. The term "nucleoside" means a glycoside compound in which a nucleobase and a reducing group of carbohydrate are bound via a glycoside binding. The term "nucleotide" is a compound in which a carbohydrate portion of the above nucleoside forms an ester with phosphoric acid, and preferably mono, di, or triphosphate.

[tRNA Including Unnatural Bases and Preparation Method Thereof]

tRNA widely exists in all living organisms and it is one of non-translated RNAs (non-coding RNAs) whose structure and function are most clear. A tRNA is composed of 76-90 nucleosides, and its secondary structure comprising three stem loops (D stem loop, anticodon stem loop, and TΨC stem loop) and one stem (acceptor stem), and forms cloverleaf like structure. Of these, the acceptor stem and the TΨC stem loop (TΨC arm) form a continuous double helix; on the other hand, the anticodon loop (anticodon arm) and the D stem loop (D arm) also form a continuous double helix likewise, thereby these two helix are orthogonal oriented to form a L-shaped tertiary structure. This L-shaped structure has a region called an anticodon consisting of three bases at one end, and this region forms a hydrogen bonds base-specifically with the codon in the mRNA. On the other hand, a region called CCA 3' terminal end exists at the other end of the L-shaped structure, and an amino acid is bound to a hydroxyl group of ribose of adenosine residue at this CCA 3' terminal end.

Figure 1:
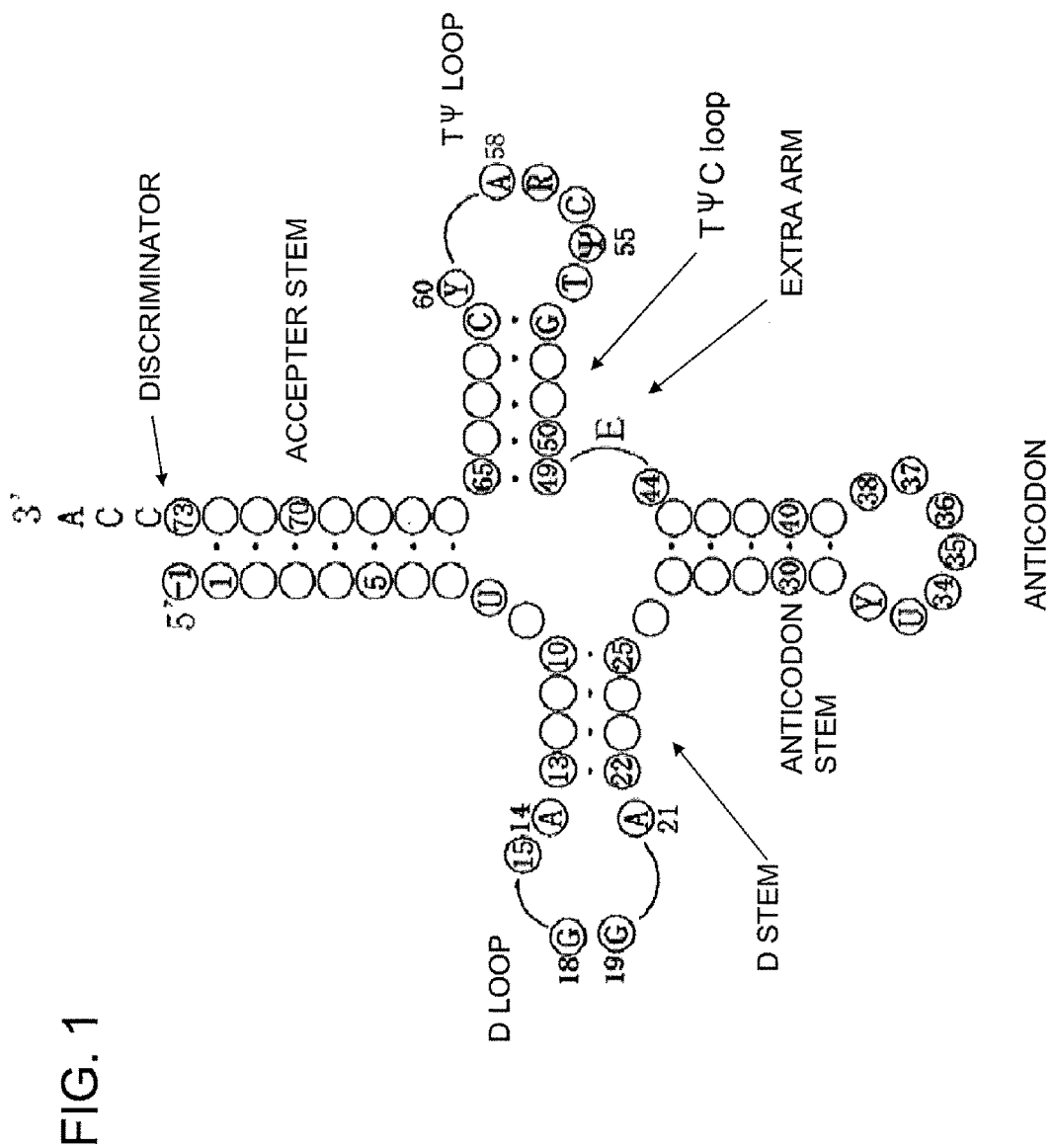
[FIG. 1] It is a schematic view showing a secondary structure of a standard tRNA.

FIG. 1 shows a secondary structure of the standard tRNA. Positions where the kind of the base is specified are "conserved residues" conserved in all of the tRNAs. In order to fix the number of these conserved residues, nucleotide residues in tRNA are numbered as shown in FIG. 1. The "anticodon" corresponds to positions 34-36 and the "discriminator" corresponds to position 73. Only for histidine tRNA, a nucleotide exists at position −1 and this nucleotide forms a base pair with the discriminator. In the present description, it is understood that the terms indicating the structure of tRNA mean general technical terms in the technical field. "A" indicates adenine, "G" guanine, "C" cytosine, "T" thymine, "U" urasil, "Y" pyrimidine and "R" purine residues, respectively. The number of residues included in the portion represented by the solid line is different depending on molecular species of tRNA. In the type II tRNA, over 10 residues of nucleotides are included in the solid line portion represented by E, and they form a stem-loop structure (it is also called as extra arm).

A specificity of pairing between codon and anticodon is supported by a base-specific hydrogen bonds; on the other hand, there exists no physical and chemical interaction to determine a specificity between tRNA and amino acid. It is understood that the aminoacyl-tRNA synthetase (aaRS) to be hereinafter described is prepared for each amino acid and this enzyme presumably recognizes precise combination of amino acid with tRNA. It is suggested that the anticodon and discriminator are recognized by the aaRS for many tRNAs based on a crystal structure analyses of a complex with the aaRS and tRNA. In addition, it is understood that a unique position(s) other than the anticodon and discriminator is recognized in each tRNA, and these positions act on identification with other tRNAs.

Therefore, in the present invention, the unnatural base is introduced into any position(s) of tRNA, preferably any position(s) other than conserved residue, thereby the modified tRNA, in which an efficiency of aminoacylation reaction is improved compared to original tRNA, can be synthesized. Here, the term "an improvement of the efficiency of aminoacylation reaction" may be either that a reaction efficiency with a targeted noncanonical amino acid rises or that a reaction efficiency with 20 kinds of standard amino acids falls.

More preferably, it is possible that an interaction site regarding a pair of a targeted aaRS and tRNA is determined and one or more base(s) at these sites of tRNA is/are replaced with (an) unnatural base(s). The residue related to amino acid specificity of tRNA is at least one position selected from a class consisting of the first three base pairs (positions 1 and 72, positions 2 and 71, positions 3 and 70) of the acceptor stem, a base pair of position 73 and the residue at position −1 in the case where a nucleotide at position −1 exists, the anticodon, the discriminator, the entire extra arm in the case of type II tRNAs, position 20, position 32, position 37, and position 38.

The unnatural base which is introduced into a desired position of these tRNAs is not particularly restricted; however, it is necessary to have a high selectivity in transcription reaction with RNA polymerase and to incorporate the unnatural base site-specifically at a position complementary to a specific base in a template DNA for synthesis by transcription reaction from a gene coding tRNA containing the unnatural base. In addition, in the case where these unnatural base are introduced into the anticodon in tRNA, it is important to be capable of specifically binding with a codon in mRNA. Moreover, it is preferred that the tRNA gene defined in the present invention can be amplified by PCR, therefor it is desired to have a high selectivity in a replication reaction by DNA polymerase.

Therefore, in a preferred mode of the present invention, any unnatural base selected from the following unnatural base pairs are listed. As a such unnatural base pair, it is a base pair of any one selected from a class consisting of 2-oxo-1H-pyridine-3-yl (y) group which may have a substituted group at position 5, 2-oxo-1H-imidazole-3-yl (z) group, 2-formyl-1H-pyrrole-1-yl (Pa) group which may have a substituted group at position 4 and 2-nitro-1H-pyrrole-1-yl (Pn) group which may have a substituted group at position 4; and any one selected from a class consisting of 2-amino-6-(2-thienyl)-9H-purine-9-yl (s) group, 7-(2-thienyl)-imidazo[4,5-b]pyridine-3-yl (Ds) group, and 9H-purine-9-yl group substituted at position 6 or at positions 2 and 6.

Further explaining some of these unnatural bases in more detail, the 2-formyl-1H-pyrrole-1-yl group which may have a substituted group at position 4 has the following structure expressed as general formula (I).

[Chemical Formula 1]

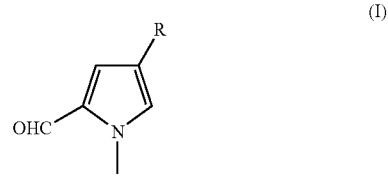

In the formula (I), the R at position 4 in pyrrole ring is hydrogen atom; alternatively, the R may be replaced with a substituted group selected from a class consisting of a substituted or non-substituted C1-C3 alkyl group, a substituted or non-substituted C2-C3 alkenyl group, or a substituted or non-substituted C2-C3 alkynyl group. The above alkyl group, alkenyl group, or alkynyl group and the like may be further replaced with one or more groups independently selected from a class consisting of lower alkyl group, halogen group, hydroxyl group, amino group, alkylamino group and heteroaromatic ring. The 2-formyl-1H-pyrrole-1-yl group which may have a substituted group at position 4 of the present invention is called "Pa" or "Pa derivative" depending on the context in the present description.

Concretely, the 2-formyl-1H-pyrrole-1-yl group which may have a substituted group at position 4 may be selected from a class consisting of:
1) 2-formyl-1H-pyrrole-1-yl (Pa) group;
2) 2-formyl-4-(1-propyne-1-yl)-1H-pyrrole-1-yl group;
3) 2-formyl-4-methyl-1H-pyrrole-1-yl group; and
4) 2-formyl-4-ethinyl-1H-pyrrole-1-yl group.
More preferably, it is 2-formyl-1H-pyrrole-1-yl group.

A nucleoside and a nucleotide having "2-formyl-1H-pyrrole-1-yl group which may have a substituted group at position 4" of the present invention can be synthesized using known methods. For example, pyrrole-2-carboaldehyde as its starting material can be purchased from Aldrich [1003-29-8] or Merck [807574]. Also, Pa derivative can be synthesized basically by derivatizing from Pa. For example, a derivative introduced propyne at position 4 in Pa is described at Bioorg. Med. Chem. Lett., 13, p. 4515-4518 (2003).

On the other hand, as the unnatural base which can form a base pair based on a specific hydrogen bond(s) with the above Pa or Pa derivative, a 9H-purine-9-yl group substituted at position 6 or positions 2 and 6 is listed, and it is expressed as the following formula (II).

[Chemical Formula 2]

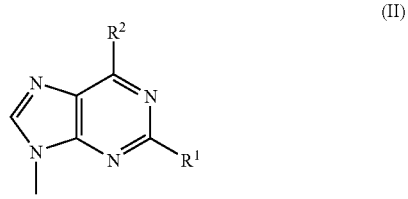

(II)

In the formula (II), $R^1$ is hydrogen atom or amino group, $R^2$ is a substituted or non-substituted 2-thienyl group or 2-thiazolyl group. The thienyl group or thiazolyl group of $R^2$ is non-substituted; alternatively, it may have one or more substituted groups at position 4 and/or position 5 independently selected from a class consisting of methyl group, amino group, nitro group, and hydroxy group. Among 9H-purine-9-yl group substituted with position 6, or positions 2 and 6 of the present invention, those whose $R^2$ is a substituted or non-substituted 2-thienyl group is called "s" or "s analog" according to a context of the present description. Among 9H-purine-9-yl group substituted with position 6, or positions 2 and 6 of the present invention, those whose $R^2$ is a substituted or non-substituted 2-thiazolyl group is called "v" or "v analog" according to a context of the present description.

Concretely, the 9H-purine-9-yl group substituted with position 6 or positions 2 and 6 may be selected from a class consisting of the following:
1) 2-amino-6-(2-thienyl)-9H-purine-9-yl group (s);
2) 6-(2-thienyl)-9H-purine-9-yl group (s');
3) 2-amino-6-(4-methyl-2-thienyl)-9H-purine-9-yl group;
4) 6-(4-methyl-2-thienyl)-9H-purine-9-yl group;
5) 2-amino-6-(5-methyl-2-thienyl)-9H-purine-9-yl group;
6) 6-(5-methyl-2-thienyl)-9H-purine-9-yl group;
7) 2-amino-6-(2-thiazolyl)-9H-purine-9-yl group (v);
8) 6-(2-thiazolyl)-9H-purine-9-yl group;
9) 2-amino-6-(4-methyl-2-thiazolyl)-9H-purine-9-yl group;
10) 6-(4-methyl-2-thiazolyl)-9H-purine-9-yl group;
11) 2-amino-6-(5-methyl-2-thiazolyl)-9H-purine-9-yl group; and
12) 6-(5-methyl-2-thiazolyl)-9H-purine-9-yl group.

More preferably, it is 2-amino-6-(2-thienyl)-9H-purine-9-yl group.

"9H-purine-9-yl group substituted with position 6, or positions 2 and 6" of the present invention, and nucleoside and nucleotide having it can be synthesized using known methods. For example, a method of synthesizing 2-amino-6-(2-thienyl)-9-(1-β-D-ribofranosyl)purine5'-triphosphate(sTP) from 2-N-phenoxyacetyl-6-(2-thienyl)-9-(2,3-di-O-acetyl-1-β-D-ribofranosyl)purine is disclosed in Example 1 of Japanese Patent Kokai No. 2007-61087 (reference document 1). The disclosure of the reference document 1 is incorporated herein by reference thereto.

In addition, for example, a synthesis of the "s" is described in the second paragraph of the second page of Bioorg. Med. Chem. Lett., 11, p. 2221-2223 (2001) (reference document 2). Also, a synthesis of "v" is disclosed in WO2005/026187 (reference document 3), at paragraphs 0026, 0027, FIGS. 5-6, and the like, for example. Alternatively, it is disclosed in J. Am. Chem. Soc., 127, p. 8652-8658 (2005) (reference document 4), paragraph in right column of page 2. The disclosures of the reference documents 2-4 are incorporated herein by reference thereto.

In a further preferred mode, as the unnatural base which can form a base pair with the above Pa or Pa derivative based on a hydrophobic interaction, there is 7-(2-thienyl)-imidazo[4,5-b]pyridine-3-yl (Ds) group. These interactions can be expressed as follows.

[Chemical Formula 3]

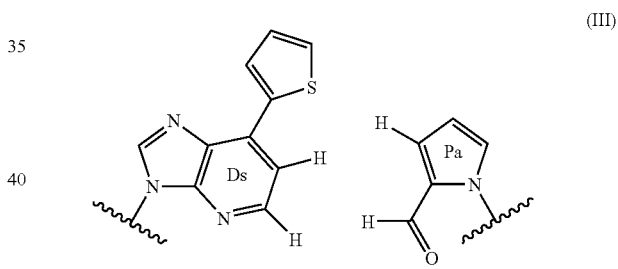

(III)

Although the above Ds-Pa pair has a specific complementation in in vitro or in vivo transcription and replication reactions, there is a problem that Ds themselves form a pair to form Ds-Ds pairs in the case of using usual Ds triphosphate as a substrate. Thus, it is preferable to use γ-amido triphosphate which is a modulatory nucleotide as a substrate of Ds in the replication reaction. An incorporation rate of the γ-amido triphosphate of Ds into a position facing Ds falls, but that of into complementary strand of Pa does not fall in the replication reaction. More preferably, the γ-amido triphosphate of adenine may be used for decreasing a misincorporation rate of adenine into complementary strand of Pa. Thus, according to use of a combination of usual nucleotide triphosphate of Pa, G, C and T with the γ-amido triphosphate of Ds and A, the replication reaction by DNA polymerase is advanced specifically, thereby it is possible to amplify DNA fragment having the Ds-Pa pair by PCR.

In a further more preferred mode, 2-nitro-1H-pyrrole-1-yl (Pn) group is listed as the unnatural base forming a base pair in the replication reaction more specifically than the above Pa. Its hydrophobic interaction can be expressed as follows.

[Chemical Formula 4]

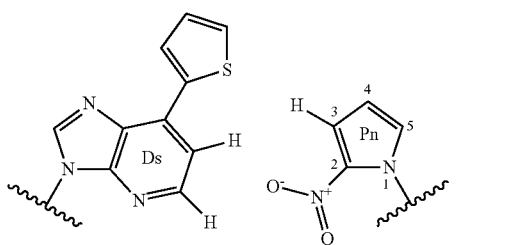

A nitro group at position 2 of Pn can efficiently suppress a mismatch with adenine (A) which is a natural base in the replication reaction. Accordingly, in PCR amplification reaction, it is possible to synthesize the Ds-Pn pair efficiently and specifically by using γ-amido triphosphate of Ds, usual triphosphate of Pn and other natural bases.

As the preparation method of the modified tRNA of the present invention, it is preferable that transcription, reverse-transcription or replication is performed from a template DNA including the above unnatural base pair and then the modified tRNA is synthesized by incorporating a nucleotide including other specific unnatural base into a complementary position of a template nucleotide including one unnatural base, without particular restriction to chemical synthesis method, enzymatic synthesis method and a method using the both and the like. It is possible to include one or several unnatural base(s) in the modified tRNA molecule.

As the complementary unnatural base pair, unnatural base pairs as the above Ds-Pa, Ds-Pn, s-y, s-z, x-y, v-y and the like are listed, without particular restriction. Among them, particularly preferred base pairs are the Ds-Pa pair and the Ds-Pn pair, and a template DNA including these base pairs are amplified by DNA replication reaction to synthesize tRNA by transcription reaction using the amplified template DNA.

[Aminoacyl-tRNA Synthetase (aaRS)]

There are 20 kinds of aaRSs corresponding to naturally-existing 20 kinds of amino acids, and each aaRS recognizes only one amino acid and one set of tRNAs (there is a case of the presence in plurality). The recognition of amino acid and tRNA with aaRS is extremely strict, it has been said that the probability of mistake of protein synthesis is around 1/10000 per one amino acid. According to the difference in ATP-binding motif, 20 kinds of aaRSs are classified into two classes (class I and class II) with 10 kinds each. Between these two classes, structures or catalytic mechanisms of catalytic domains are different. The class I aaRSs transfer an amino acid to the 2'OH of the ribose of the adenosine residue at the 3' terminal end of the corresponding tRNA; on the other hand, the class II enzymes bind an amino acid to the 3'OH. It has been said for the recognition mechanism of tRNA that the class II aaRSs strongly recognize the acceptor stem of tRNA; on the other hand, the class I aaRSs recognize a wider portion including the D arm on the tRNA.

The aaRS(s) used in the present invention may be any naturally existing aaRS, but preferably it is a mutant enzyme which can activate the noncanonical amino acid. A protein containing the noncanonical amino acid (allo-protein) is useful for protein function and structure analysis, and further it provides very important technical base for synthesizing new bioactive substance or high-performance nano-device. In order to produce such an allo-protein, it is necessary to synthesize aaRS such that recognizes the noncanonical amino acid and also recognizes tRNA unrecognizable with other aaRSs (for example, a suppressor tRNA corresponding to stop codon). So far, it has been reported that tyrosyl-tRNA synthetase (TyrRS) of E.coli was modified to various mutant TyrRSs for recognizing specifically various tyrosine derivatives and amber-suppressor tRNA which are unrecognizable with the wild-type enzyme (please see, for example, Kiga, D. et al., Proc. Natl. Acad. Sci. USA, 23, 9715-9720 (2002) (reference document 5)). In addition, pyrolysyl-tRNA synthetase (PylRS) derived from archaebacterium and a mutant enzyme thereof can introduce pyrolysine and its derivative into a protein (please see Japanese Patent Kokai No. 2007-037445 (reference document 6)). The disclosures of the reference documents 5 and 6 are incorporated herein by reference thereto.

Phosphoseryl-tRNA synthetase (SepRS) and its mutant enzyme obtained from an archaebacterium, especially methanogenic archaebacterium can be used for introducing phosphoserine in E.coli or eukaryotic cell. For example, the wild-type SepRS can be obtained from Methanosarcina mazei, Methanococcus maripaludis and Methanocaldococcus jannaschii as methanogenic archaebacterium or Archaeoglobus fulgidus as sulfur reduction archaebacterium and the like, but it is not restricted to these. Many bacterial genomic DNA sequences including these archaebacterium are known, it is possible to obtain other homologous gene by performing a homology search of DNA sequence from a public data base like as GenBank and the like, for example. As a typical example, SepRS derived from Methanosarcina mazei is registered with GenBank accession no. NC_003901, SepRS derived from Methanococcus maripaludis is registered with GenBank accession no. NC_005791, SepRS derived from Methanocaldococcus jannaschii is registered with GenBank accession no. NC_000909, and SepRS derived from Archaeoglobus fulgidus is registered with GenBank accession no. NC_000917 (GeneID: 1483322). The base sequence of SepRS gene derived from the above Archaeoglobus fulgidus is shown in SEQ ID 1, the amino acid sequence of the protein is shown in SEQ ID 2. These SepRS sequences are well-conserved, for example, the amino acid sequence homology is about 70% or above.

Based on the wild-type aaRS structure, various mutant enzymes can be designed by replacing, deleting or adding amino acid residues at a desired position(s). For example, a ternary complex structure of SepRS-tRNA$^{Cys}$-phosphoserine is known. The atomic coordinate obtained from respective 2.6 Å and 2.8 Å resolutions of SepRS-tRNA$^{Cys}$-Sep ternary complex and SepRS-tRNA$^{Cys}$ binary complex are registered with the code numbers as respective 2DU3 and 2DU4 in the protein data bank (PDB, Protein Data Bank, managed by The Research Collaboratory for Structual Bioinformatics (RCSB), (reference document 7)). The disclosure of the reference document 7 is incorporated herein by reference thereto.

Inventors of the present invention have already obtained a mutant SepRS, in which a binding affinity against the amber suppressor and the opal suppressor tRNA of tRNA$^{Cys}$ is increased based on the above structure (for example, please see the above non-patent document 4). The disclosure of the reference document 4 is incorporated herein by reference thereto.

In a preferred mode of the present invention, a triple mutant SepRS (E418N, E420N, T423V), in which glutamic acid at positions 418 and 420 in amino acid sequence shown as SEQ ID 2 are replaced with asparagine and threonine at position 423 in the amino acid sequence is replaced with valine, can be used for the allo-protein synthesis in combination with tRNA containing the above unnatural base. Various known methods for a person skilled in the art can be used for a method to synthesize such a mutant. For example, by using a primer in which a base sequence coding a position of targeted amino acid is replaced with a base sequence coding the amino acid to be modified, a DNA coding the full length mutant SepRS is obtained by PCR amplification with the DNA having a substituted base sequence coding the amino acid to be modified, thereby an expression is possible from this DNA using a host cell like E.coli and the like. Alternatively, it can be performed with the known site-specific mutagenesis method such as Kunkel method or Gapped duplex method and the like, and the mutagenesis kit (for example, Mutan-K or Mutan-G (TAKARA) and the like) using these methods can be used.

[Screening Method of the Modified tRNA]

Further, according to the present invention, there is provided a method of screening a modified tRNA for improving aminoacylation reaction of tRNA by a noncanonical amino acid. This method comprises:
(a) preparing a suppressor tRNA recognized by an aminoacyl-tRNA synthetase which can activate the noncanonical amino acid;
(b) synthesizing the modified tRNA containing an unnatural base at any position(s) in the tRNA;
(c) measuring an aminoacylation activity of the modified tRNA under existence of standard and noncanonical amino acids and the aminoacyl-tRNA synthetase corresponding to these amino acids; and
(d) selecting the modified tRNA, in which an incorporation amount of the noncanonical amino acid is increased or an incorporation rate of the noncanonical amino acid is improved compared to that of the standard amino acid.

Here, in the case of designing into which position(s) of tRNA the unnatural base(s) is introduced, as mentioned the above, the interaction position is determined about a pair of a targeted aaRS and RNA, and then it is possible to replace one or more bases for these positions of tRNA into unnatural base(s). A residue relating to amino acid specificity of tRNA is at least one position selected from the first three base pairs (positions 1 and 72, positions 2 and 71, positions 3 and 70) of the acceptor stem, (in the case of existence of nucleotide at position −1) a base pair of this residue (position −1) and position 73, the anticodon, the discriminator, the entire extra arm regarding type II tRNA, position 20, position 32, position 37 and position 38.

It is preferred for the synthesis of the modified tRNA in the above process (b) to prepare a tRNA gene including the unnatural base pair and to perform replication and transcription reactions with the tRNA gene as a template DNA. As the unnatural base pair which can be used for such a modified tRNA synthesis, it is preferred for the base pair of any one selected from 2-oxo-1H-pyridine-3-yl (y) group which may have a substituted group at position 5, 2-oxo-1H-imidazole-3-yl (z) group, 2-formyl-1H-pyrrole-1-yl (Pa) group which may have a substituted group at position 4 and 2-nitro-1H-pyrrole-1-yl (Pn) group which may have a substituted group at position 4, and any one of 7-(2-thienyl)-imidazo[4,5-b] pyridine-3-yl (Ds) group and 9H-purine-9-yl group. Among them, especially preferred is the Ds-Pa pair or the Ds-Pn pair.

Alternatively, a gene library of tRNA, in which the unnatural base is introduced at any positions randomly other than related positions interacting to the above aaRS, is synthesized, and then the above screening may be performed using this modified tRNA library. This is because that tRNA has a folded structure and its bases are involved in a three-dimensionally interaction network, so that an effect of the base substitution extends to a remote position even without a direct interaction with the aaRS.

[Synthesis of a Protein Incorporating the Noncanonical Amino Acid]

A production method of a protein containing a noncanonical amino acid according to the present invention is characterized by: the following expressions (a) (b) and (c) in a cell(s) or in a cell extract solution under existence of unnatural bases and noncanonical amino acids:
(a) an aminoacyl-tRNA synthetase which can activate the noncanonical amino acid;
(b) a modified tRNA of the present invention recognized by the aminoacyl-tRNA synthetase; and
(c) an mRNA coding a desired protein having a codon including a nonsense codon or the unnatural base at a desired position(s).

Here, as a synthetic system of the aaRS or the modified tRNA related to the present invention, any expression system can be used, without particular restriction. For example, a cell-free protein synthesizing system and a protein synthesizing system in eubacterium cells, or an eukaryote cell, preferably an animal cell, especially preferably a mammalian cell are listed.

The cell-free protein synthesizing system is a system that takes out the protein factor which is necessary for translation of the protein as cell extract solution, and synthesizes an aimed protein by re-constituting this reaction in a test tube. The cell-free system can be constituted by using an extract derived from various biological species, for example, extracts can be prepared from bacterium like E.coli and thermophilic bacteria and the like, wheat germ agglutinin, rabbit reticulocyte, mouse L-cell, Ehrlich ascites tumor cell, HeLa cell, CHO cell and budding yeast, and the like by using well-known techniques. Among them, it is preferred to use an extract from E.coli, for example, an S30 extract prepared by methods described in Zubay et al. (Zubay et al., Ann. Rev. genet. Vol. 7, pp. 267-287 (1973) (reference document 8)) and Pratt et al. (Pratt, J. M. et al., Transcription and Translation—A Practical Approach, (1984), pp. 179-209, Henes, B. D. et al. eds., IRL Press, Oxford (reference document 9)) can be used. Note, the contents of reference documents 8 and 9 are incorporated herein by reference thereto.

When the synthesis reaction of the protein incorporating noncanonical amino acid is performed, a DNA or mRNA coding a desired protein having a nonsense codon or a codon including the unnatural base at a desired position in a template of transcription/translation is added to the above cell extract solution. In addition, the noncanonical amino acid, the aminoacyl-tRNA synthetase which can activate the noncanonical amino acid, the modified tRNA of the present invention and nucleotide triphosphate including the unnatural base included in the modified tRNA are added. Furthermore, it is possible to include an energy source, various ion, buffer solutions, ATP regenerating system, nuclease inhibitor, tRNA, reducing agent, polyethylene glycol, cAMP, folic acid or the like, antibiotic, substrate for RNA synthesis in the case of using DNA as a template, and RNA polymerase and the like.

These are appropriately selected depending on the targeted protein or kinds of protein synthesizing system for using, and to be prepared. For example, in the case of E.coli S30 extract, a part of or all of the following is added: Tris-acetate, DTT, NTPs(ATP, CTP, GTP and UTP), phosphoenolpyruvate, pyruvate kinase, amino acids(phosphoserine is added in addition to 20 kinds of natural amino acids), polyethylene glycol (PEG), folic acid, cAMP, tRNA, ammonium acetate, potassium acetate, potassium glutamate, and magnesium acetate with optimum concentration and the like.

Figure 2:
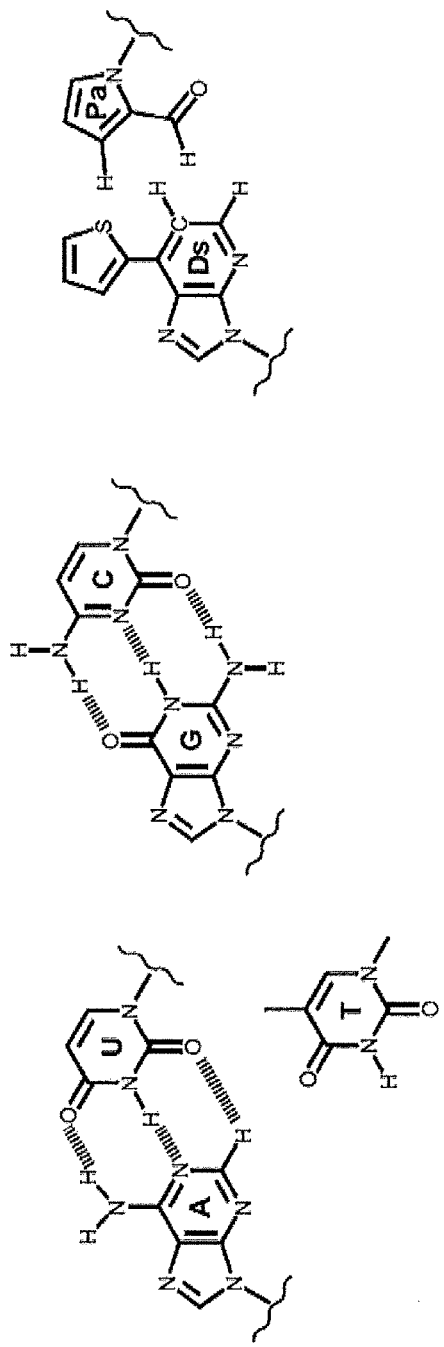
[FIG. 2] It shows the unnatural base pairs system for the gene code extension. (A) Structures of natural A-T(U) and G-C base pairs, and the unnatural Ds-Pa base pair. (B) It represents base pairs of codon-anticodon of tRNAs used in Example.
Figure 2:
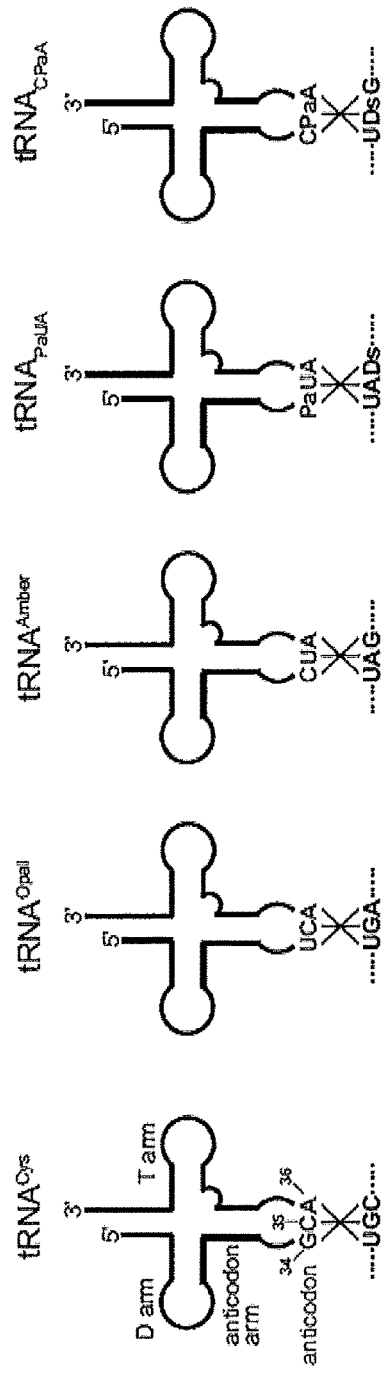

Next, for explaining the present invention in more detail, the following examples, in which phosphoserine is linked to the modified tRNA including Pa group at a position of anticodon with using the unnatural base pair of the Ds-Pa pair shown in FIG. 2, will be indicated. However, the present invention is not particularly restricted by these examples.

EXAMPLE 1

[Synthesis of tRNA$_{PaUA}$ and tRNA$_{CPaA}$]
(1) Preparation of tRNA Molecule Including the Unnatural Base With Applied Biosystems 392 DNA synthesizer, a DNA fragment as a template was chemically synthesized using Ds and phosphoamidite (Applied Biosystems) as a natural base and 2'-O-methylribonucleosidoamidite (Glen Research). Its base sequence of the DNA fragment is as follows.

```
5'-non-template DNA fragment (71 bases):
                                    (SEQ ID 3)
5'-GATAATACGACTCACTATAGCCAGGGTGGCAGAGGGGCTATGC

GGCGGACTCTAGATCCGCTTTACCCGG-3'

5'-template DNA fragment (tRNA_PaUA, 60bases):
                                    (SEQ ID 4)
TmGmGAGCCAGGGCCCGGATTCGAACCGGGGTAAAGCGGATCTADs

AGTCCGCCGCATAGCCC-3'

5'-template DNA fragment (tRNA_CPaA, 60bases):
                                    (SEQ ID 5)
TmGmGAGCCAGGGCCCGGATTCGAACCGGGGTAAAGCGGATCTDsG

AGTCCGCCGCATAGCCC-3'
```

Here, Tm represents 2'-O-methylthymidine, Gm represents 2'-O-methylguanosine. A double-stranded DNA template (94 base pairs) was prepared such that the 5'-non-template DNA fragment (SEQ ID 3) and the 5'-template DNA fragment (SEQ ID 4 or 5) were annealed, then a primer extension reaction was performed with Klenow fragment (Takara Bio). A tRNA transcript including Pa was synthesized at 37° C. with T7RNA polymerase (2.5 units/μl) for 6 hours using 0.5 μM template in a solution including 40 mM TrisHCl, 24 mM MgCl$_2$, 0.01% Triton, 2 mM spermidine, 5 mM dithiothreitol, 3 mM PaTP, 1 mM natural NTPs and 10 mM GMP. The transcript was purified with polyacrylamide gel electrophoresis.

(2) Nucleotide composition analysis of T7 transcript

A transcription reaction was performed under existence of [α-32P]ATP (2 μCi) or [α-32P]UTP(2 μCi) for analyzing. The transcript was digested at 37° C. with RnaseT2 (0.75-1.5 units/μl) for 1-2 hours in a solution (10 μl) including 15 mM sodium acetate buffer (pH 4.5). Using Merck I-IPTLC plate (100×100 mm) (Merck), the digested material was analyzed with two-dimensional TLC using a one-dimensional developing solvent (isobutyl acid: HCl: water (volume ratio 66:1:33)) and a two-dimensional developing solvent (isopropyl alcohol:HCl:water (volume ratio 70:15:15)). A product on the TLC plate was analyzed with Image analyzer BAS2500 (Fuji film). A quantification of each spot was calculated to obtain an average of 3-9 data sets.

(3) Result

In order to investigate aminoacylation by a series of mutant SepRSs having 1-3 point mutations within the anticodon recognition site, two tRNA molecules: tRNA$_{PaUA}$ and tRNA$_{CPaA}$, including PaUA or CPaA sequences in its anticodon by a transcription reaction via the above described unnatural Ds-Pa base pair were synthesized (refer to FIG. 2B and FIG. 3A). Compared to tRNA$^{Amber}$, the first or the second nucleotide in the anticodon triplets was replaced with Pa for these two tRNA molecules.

tRNA$_{PaUA}$ and tRNA$_{CPaA}$ (75 bases each) were prepared with T7RNA polymerase using Pa substrate (PaTP) and a template DNA including Ds. As shown in FIG. 3B, the template DNA (94 base pairs) of mRNA was constructed through a primer extension reaction of a partial double-stranded DNA formed of 5'-non-template DNA fragment (71 bases) and 5'-template DNA fragment (60 bases). Two nucleotides (G and T) at the 5' terminal end of the template strand were replaced with 2'-O-methylribonucleoside thereof (Gm and Tm). This can decrease an addition of one or more non-template nucleotide(s) at the 3' terminal end of a new transcript. The transcription reaction was performed using 3 mM PaTP, 1 mM natural NTPs and 10 mM GMP and 0.5 μM template. The concentration of PaTP was increased to 3 mM because an incorporation of PaTP is somewhat less efficient compared to that of natural NTPs.

It was confirmed by the nucleotide composition analysis of the transcription product with internal label that Pa was incorporated into the tRNA transcript at a position facing to Ds in the template DNA with high selectivity. Its result is shown in FIG. 3C and Table 1. In the analysis of tRNA$_{PaUA}$, a spot corresponding to a radiolabeled ribonucleoside 3' phosphate equivalent to Pa appeared on the two-dimensional TLC obtained from the transcript labeled with [α-$^{32}$P]UTP, but there was no spot in the case of using [α-$^{32}$P]ATP. This result indicates a correct incorporation of Pa into the position facing to Ds. This is because that 3'-phosphate of Pa is radiolabeled only in the case of using [α-$^{32}$P]UTP in the transcriptional reaction when a neighboring base at the 3' side of Pa is U in the tRNA sequence. On the other hand, since no spot of Pa has been detected on the TLC of the transcriptional product of the tRNA$_{PaUA}$ labeled with [α-$^{32}$P]ATP, it is indicated that a misincorporation of Pa into a complementary position of a natural base hardly happen in the transcription reaction using 3 mM PaTP and 1 mM natural NTPs. Similarly, in the analysis of tRNA$_{CPaA}$, a spot of phosphorylated Pa is recognized on the TLC obtained from the transcription product labeled with [α-$^{32}$P]ATP, but it was not detected in the case of labeling [α-$^{32}$P]UTP. This is because that a neighboring base at the 3' side of Pa is A in the tRNA$_{CPaA}$ and radiolabeled only with [α-$^{32}$P]ATP.

TABLE 1

| item number | tRNA | [α-$^{32}$P] NTP | nucleotide composition$^a$ incorporated at 5' side of U or A | | | | |
|---|---|---|---|---|---|---|---|
| | | | Ap | Gp | Cp | Up | Pap |
| 1 | tRNA$_{PaUA}$ | ATP | 1.021$^b$ [1]$^c$ (0.035)$^d$ | 4.046 [4] (0.042) | 2.889 [3] (0.044) | 3.032 [3] (0.021) | 0.012 [0] (0.002) |
| 2 | tRNA$_{PaUA}$ | UTP | 2.901 [3] (0.023) | 1.996 [2] (0.038) | 4.936 [5] (0.030) | 3.183 [3] (0.021) | 0.984 [1] (0.006) |

TABLE 1-continued

| | | | nucleotide composition[a] incorporated at 5' side of U or A | | | | |
|---|---|---|---|---|---|---|---|
| item number | tRNA | [α-32P] NTP | Ap | Gp | Cp | Up | Pap |
| 3 | tRNA$_{CPaA}$ | ATP | 1.042 [1] (0.029) | 3.937 [4] (0.059) | 2.962 [3] (0.059) | 2.081 [2] (0.052) | 0.978 [1] (0.010) |
| 4 | tRNA$_{CPaA}$ | UTP | 2.977 [3] (0.098) | 1.969 [2] (0.035) | 4.994 [5] (0.048) | 3.049 [3] (0.109) | 0.011 [0] (0.001) |

Figure 3:
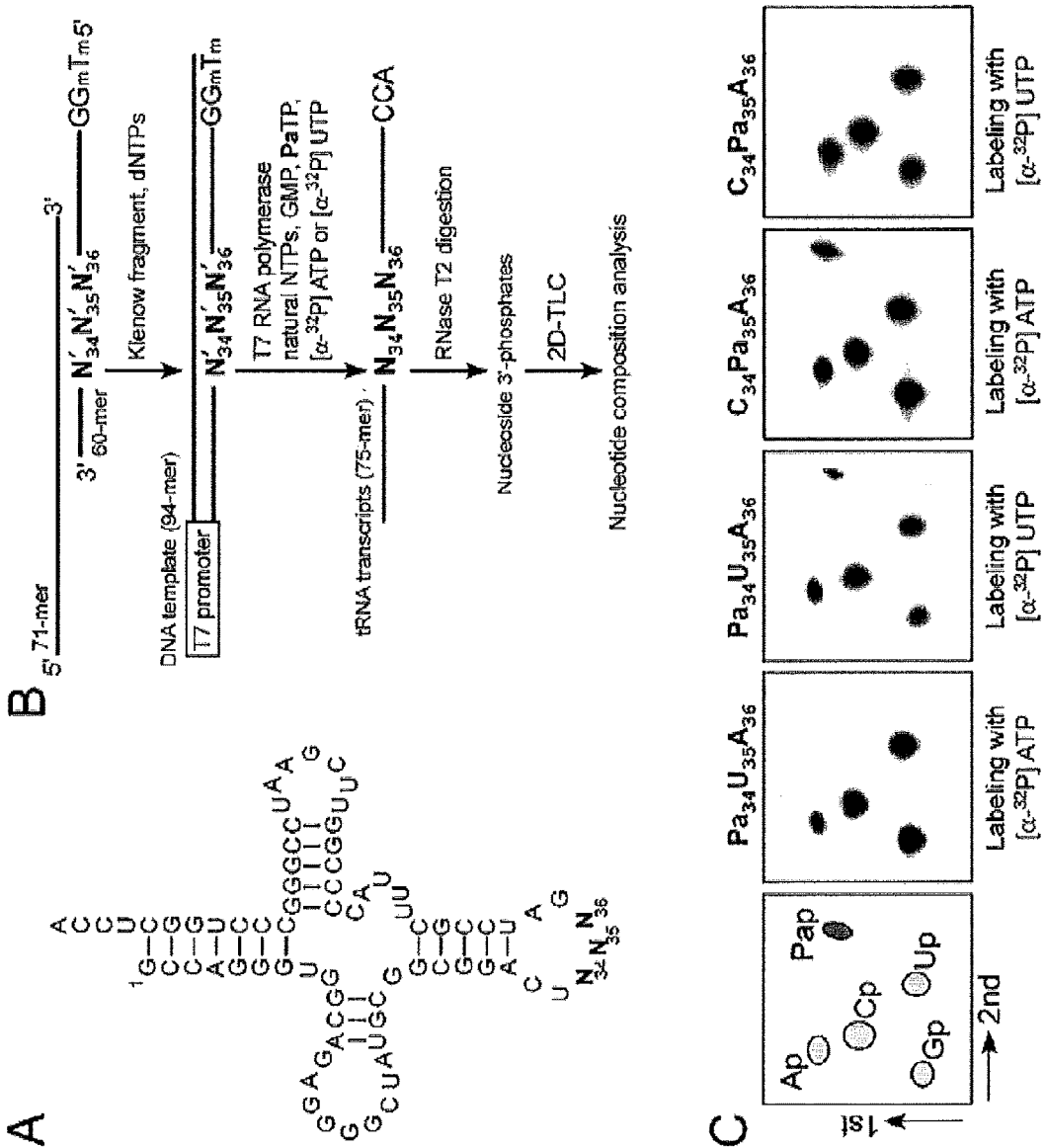
[FIG. 3] It shows the specific T7 transcription reaction via the Ds-Pa base pair formation for $tRNA_{PaUA}$ and $tRNA_{CPaA}$ synthesis. (A) Structure of tRNA used in Example. (B) Schemes of $tRNA_{PaUA}$ and $tRNA_{CPaA}$ synthesis, and nucleotide component analysis. (C) A result of two dimensional TLC analysis of labeled nucleotide after RNaseT2 treatment of a transcript production.

Note
[a] As shown in FIG. 3, it shows nucleotide composition incorporated at 5' neighboring base of A (item numbers 1 and 3) or U (item numbers 2 and 4).
[b] The values were determined by a calculating formula as follows: (radioactivity of each nucleotide)/[all radioactivity of all nucleotide (3'-phosphate)] × (all numbers of 5' neighboring base of [α-32P]NTP)
[c] Theoretical value of each nucleotide is shown in each parenthesis [ ].
[d] Standard deviation is shown in each parenthesis ( ).

According to the quantification result of these spots on TLC, a selectivity of the incorporation of Pa into a position facing Ds was about 98% in both of tRNA$_{PaUA}$ and tRNA$_{CPaA}$ (see Table 1, item numbers 2 and 3). On the other hand, a misincorporation value of PaTP facing a natural base was 1.1-1.2% (see Table 1, item numbers 1 and 4). These values indicate that the misincorporation of Pa in the tRNA transcript by the following calculating formula is 0.08-0.11% per each position of transcript:

[Pa composition]/[total number of neighboring base at 5' side of A regarding tRNA$_{PaUA}$, or total number of neighboring base at 5' side of U regarding tRNA$_{CPaA}$]×100(%)

Accordingly, by increasing PaTP concentration (3 mM) compared with natural NTPs concentration (1 mM), it was possible to introduce Pa into a position in tRNA anticodon facing the template Ds with high selectivity and efficiently, without the misincorporation of Pa into other position in the transcription product.

[Enzyme Screening for Introducing Phosphoserine into tRNA$_{PaUA}$ and tRNA$_{CPaA}$]

Various mutant SepRSs in which one or more mutations was/were introduced into amino acid residue(s) involved in relating to an interaction with the first and second anticodon bases were designed based on a ternary complex structure of SepRS-tRNA$^{Cys}$-phosphoserine of A. fulgidus. A phosphoserine binding reaction with various mutant SepRSs was performed in 100 mM HEPES-NaOH buffer solution (pH7.6) (10 μl) including 20 mM MgCl$_2$, 150 mM NaCl, 5 mM ATP, 60 μM [$^{14}$C]phosphoserine, 1 μM SepRS enzyme and 20 μM tRNA$_{PaUA}$ or tRNA$_{CPaA}$ at 50° C. After 10 minutes reaction, a reaction mixture solution (7 μl) was extracted, the reaction was terminated on a filter paper (Whatman, 3 mm) equilibrated with 10% trichloroacetic acid (TCA). The filter paper was washed three times with 5% ice-cold TCA solution, then it was washed once with 100% ethanol. A radioactivity of [$^{14}$C]Sep-tRNA precipitated on the filter paper was measured with a scintillation counter. Each experiment was repeated three times, the results were indicated by averages thereof. The results were shown in FIG. 4.

Figure 4:
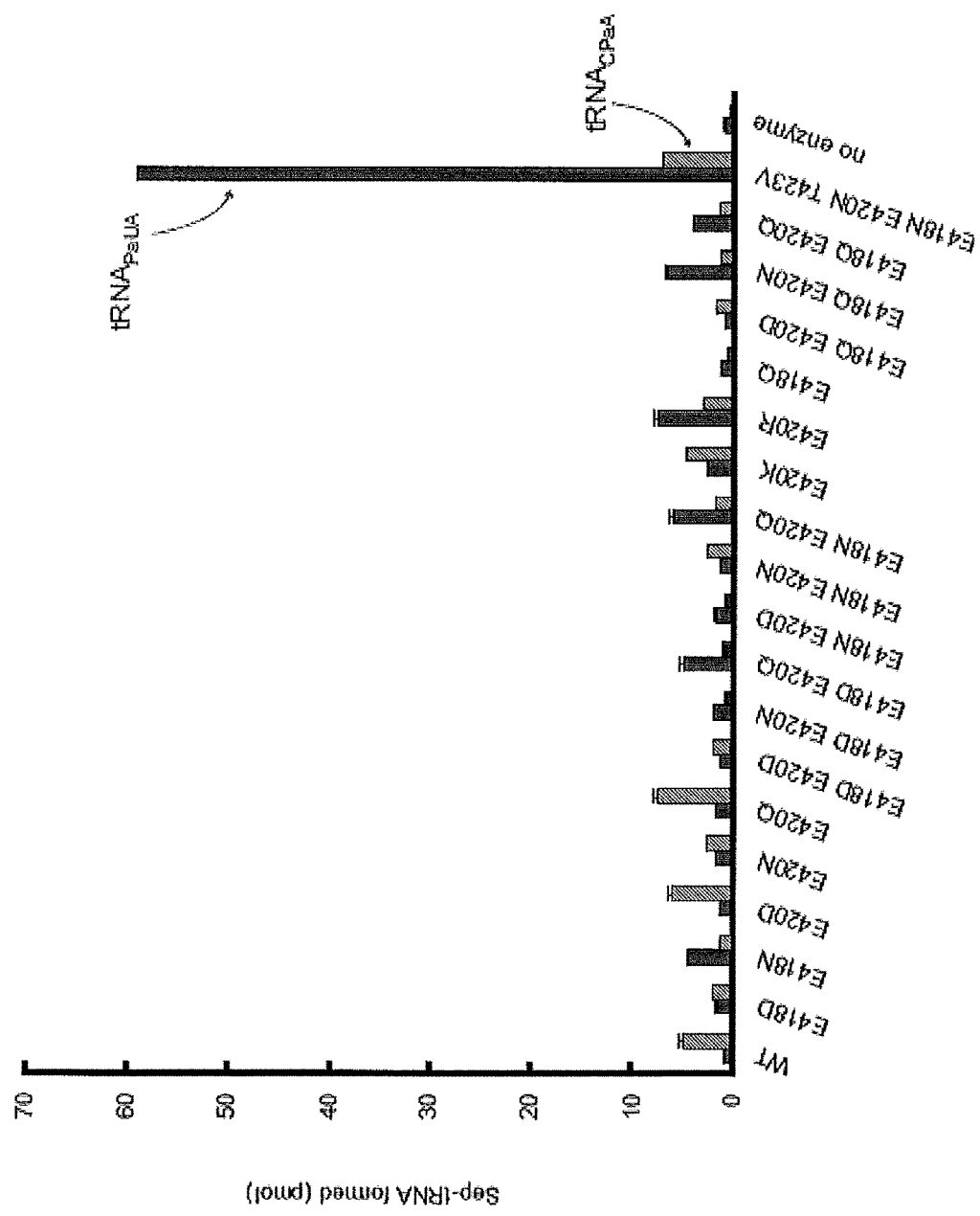
[FIG. 4] It shows a phosphoserine aminoacylation activity with various SepRS enzymes against $tRNA_{PaUA}$ and $tRNA_{CPaA}$.

As shown in FIG. 4, for most of the wild-type and mutant SepRSs having one or two point mutations, there was no indication of any measurable activity toward either tRNA$_{PaUA}$ or tRNA$_{CPaA}$. Contrary to this, there was an indication of an actual activity against tRNA$_{PaUA}$ for the triple mutant as the SepRS (E418N, E420N, T423V). This mutant enzyme also shows a detectable activity against tRNA$_{CPaA}$. It is understood for this mutant enzyme that tRNA$^{opal}$ and tRNA$^{amber}$ are aminoacylated with phosphoserine. Comparing respective phosphoseryl-tRNA amount produced under the same reaction conditions, contrary to about 60 pmol of Sep-tRNA$^{Cys}$ produced by the wild-type SepRS, Sep-tRNA$^{Cys}$ produced by the SepRS (E418N, E420N, T423V) was about 15 pmol, that of Sep-tRNA$^{opal}$ was about 30 pmol, that of Sep-tRNA$^{amber}$ was about 25 pmol, that of Sep-tRNA$_{PaUA}$ was about 60 pmol, that of Sep-tRNA$_{CPaA}$ was about 7 pmol. Therefore, the activity of the SepRS (E418N, E420N, T423V) was relatively high at tRNA$_{PaUA}$ and relatively low at tRNA$_{CPaA}$, compared to tRNA$^{opal}$ and tRNA$^{amber}$.

In order to introduce site-specifically the noncanonical amino acid into a protein using the mutant aaRS, it is required that the aaRS recognizes only exogenous tRNA specifically but does not recognize endogenous tRNA. In this regard, because there was no indication for the SepRS (E418N, E420N, T423V) about a detectable activity against an endogenous tRNA mixtures of E.coli, wheat germ and yeast, it is conceived that tRNA$_{PaUA}$ is highly specifically aminoacylated.

[Measurement of Enzymatic Activity and Kinetic Analysis]

The kinetic analysis of the phosphoserine binding reaction was performed in a 100 mM HEPES-NaOH buffer solution (pH7.6) (15 μl) including 20 mM MgCl$_2$, 150 mM NaCl, 5 mM ATP, 100 μM [$^{14}$C] phosphoserine, 1,2,5,10,20,40,80 or 100 [M tRNA (tRNA$^{Cys}$, tRNA$^{Opal}$, tRNA$^{Amber}$, tRNA$_{PaUA}$ or tRNA$_{CPaA}$) and SepRS enzyme at 50° C. In order to determine the kinetic parameter of tRNA$^{Cys}$, 1 μM wild-type SepRS or 2 μM SepRS (E418N, E420N, T423V) was used; and 2 μM SepRS (E418N, E420N, T423V) was used for determining the kinetic parameter of tRNA$^{Opal}$, tRNA$^{Amber}$ and tRNA$_{PaUA}$; and 5 μM SepRS (E418N, E420N, T423V) was used for determining the kinetic parameter of tRNA$_{CPaA}$. When 30 seconds and 60 seconds passed after starting the reaction, a certain amount (6 μl) of a reaction mixture solution was extracted and the produced [$^{14}$C]Sep-tRNA was quantified using the same method in the above. The kinetic parameter was calculated using Eadie-Hofstee plot.

Its result is shown in the following Table 2. Compared to the kcat/Km of the wild-type SepRS against tRNA$^{Cys}$, the kcat/Km value of SepRS (E418N, E420N, T423V) against tRNA$_{PaUA}$ was decreased only to about a half, which was almost 2 fold greater than those values of SepRS (E418N, E420N, T423V) against tRNA$^{Opal}$ and tRNA$^{Amber}$. In addition, compared to the original tRNA$^{Cys}$, it is understood that the kcat/Km value of SepRS (E418N, E420N, T423V) against the tRNA$_{PaUA}$ after the modification is increased to almost 9 fold.

TABLE 2

|  | Km (μM) | kcat (s$^{-1}$) | kcat/Km | kcat/Km (relative value) |
|---|---|---|---|---|
| SepRS(wild-type):tRNA$^{Cys}$ | 26.9 | 0.115 | 0.0043 | 1 |
| SepRS(E418N E420N T423V):tRNA$^{Cys}$ | 37.2 | 0.008 | 0.0002 | 0.053 |
| SepRS(E418N E420N T423V):tRNA$^{Opal}$ | 73.3 | 0.067 | 0.0009 | 0.215 |
| SepRS(E418N E420N T423V):tRNA$^{Amber}$ | 116.6 | 0.123 | 0.0011 | 0.247 |
| SepRS(E418N E420N T423V):tRNA$_{PaUA}$ | 47.1 | 0.151 | 0.0020 | 0.476 |
| SepRS(E418N E420N T423V):tRNA$_{CPaA}$ | 48.0 | 0.013 | 0.0002 | 0.038 |

INDUSTRIAL APPLICABILITY

It is applicable for wide variety of applications and practical use not only in basic study but also in medical, in agricultural, further in industrial fields as a new material and the like to produce a protein containing the noncanonical amino acid. The present invention provides new combinations of the modified tRNA with aminoacyl-tRNA synthetase for this purpose.

Here, it is to be noted that the disclosures of the above mentioned Patent Documents etc. are all incorporated herein in their entireties by reference thereto. It should be noted that changes and modifications of the modes or examples may be done within the entire disclosure (inclusive of the claims) of the present invention and on the basis of the basic technical concept thereof. Also, it should be noted that a variety of combinations or selections of various elements as disclosed may be made within the scope of the claims of the present invention. That is, it should be noted that the present invention also includes various changes and modifications which can be made by a person skilled in the art on the basis of the entire disclosure (inclusive of the claims) and technical concept.

The invention claimed is:

1. A method of screening a modified tRNA for improving aminoacylation reaction of a tRNA by a noncanonical amino acid, comprising:

(a) preparing a modified suppressor tRNA comprising an unnatural base at the first or the second position of the anticodon of a suppressor tRNA, wherein said unnatural base comprises a 2-oxo-1H-pyridine-3-yl (y) group which may have a substituted group at position 5, a 2-oxo-1H-imidazole-3-yl (z) group, a 2-formyl-1H-pyrrole-1-yl (Pa) group which may have a substituted group at position 4 or a 2-nitro-1H-pyrrole-1-yl (Pn) group which may have a substituted group at position 4;

(b) measuring an aminoacylation activity of the modified tRNA with standard and noncanonical amino acids, and a mutant aminoacyl-tRNA synthetase that is:

a mutant aminoacyl-tRNA synthetase having the amino acid sequence of SEQ ID NO: 2 in which the glutamic acid at position 418 is replaced with aspartic acid, asparagine or glutamine;

a mutant aminoacyl-tRNA synthetase having the amino acid sequence of SEQ ID NO: 2 in which the glutamic acid at position 420 is replaced with aspartic acid, asparagine, glutamine, lysine or arginine;

a mutant aminoacyl-tRNA synthetase having the amino acid sequence of SEQ ID NO: 2 in which the glutamic acid at position 418 is replaced with aspartic acid, asparagine or glutamine, and the glutamic acid at position 420 is replaced with aspartic acid, asparagine or glutamine; or a mutant aminoacyl-tRNA synthetase having the amino acid sequence of SEQ ID NO:2 in which the glutamic acid at position 418 is replaced with asparagine, the glutamic acid at position 420 is replaced with asparagine and the threonine at position 423 is replaced with valine; and (c) selecting the modified tRNA, in which an incorporating amount of the noncanonical amino acid(s) is increased or an incorporating rate of the noncanonical amino acid is improved compared to that of the standard amino acid(s), as a modified tRNA having improved aminoacylation activity with a noncanonical amino acid.

2. The method of claim 1, wherein said modified tRNA in (a) is synthesized such that a tRNA gene including the unnatural base is prepared and a transcription reaction is performed with said tRNA gene as a template DNA.

3. The method of claim 1, wherein said unnatural base pair is a Ds-Pa pair, a Ds-Pn pair or a s-y pair.

4. A method for producing a protein incorporating a noncanonical amino acid, comprising expressing in a cell(s) or providing in a cell extract the following (a), (b) and (c) together with an unnatural base(s) and the noncanonical amino acid(s):

(a) a mutant aminoacyl-tRNA synthetase that is:

a mutant aminoacyl-tRNA synthetase having the amino acid sequence of SEQ ID NO: 2 in which the glutamic acid at position 418 is replaced with aspartic acid. asparagine or glutamine;

a mutant aminoacyl-tRNA synthetase having the amino acid sequence of SEQ ID NO: 2 in which the glutamic acid at position 420 is replaced with aspartic acid, asparagine, glutamine, lysine or arginine;

a mutant aminoacyl-tRNA synthetase having the amino acid sequence of SEQ ID NO: 2 in which the glutamic acid at position 418 is replaced with aspartic acid. asparagine or glutamine, and the glutamic acid at position 420 is replaced with aspartic acid, asparagine or glutamine; or a mutant aminoacyl-tRNA synthetase having the amino acid sequence of SEQ ID NO: 2 in which the glutamic acid at position 418 is replaced with asparagine, the glutamic acid at position 420 is replaced with asparagine and the threonine at position 423 is replaced with valine;

(b) a modified suppressor tRNA comprising an unnatural base at the first or the second position of the anticodon of a suppressor tRNA, wherein said unnatural base comprises a 2-oxo-1H-pyridine-3-yl (y) group which may have a substituted group at position 5, a 2-oxo-1H-imidazole-3-yl (z) group, a 2-formyl-1H-pyrrole-1-yl (Pa) group which may have a substituted group at position 4 or a 2-nitro-1H-pyrrole-1-yl (Pn) group which may have a substituted group at position 4 and that is recognized by said mutant aminoacyl-tRNA synthetase; and (c) an mRNA coding for a desired protein and having a nonsense codon or a codon including an unnatural base at a desired position(s), wherein said unnatural base comprises a 2-oxo-1H-pyridine-3-yl (y) group which may have a substituted group at position 5, a 2-oxo-1H-imidazole-3-yl (z) group, a 2-formyl-1H-pyrrole-1-yl (Pa) group which may have a substituted group at position 4 or a 2-nitro-1H-pyrrole-1-yl (Pn) group which may have a substituted group at position 4.

5. The method of claim 4, wherein said noncanonical amino acid is phosphoserine, pyrrolidine, lysine derivative or tyrosine derivative.

6. The method of claim 4, wherein said aminoacyl-tRNA synthetase is a mutant phosphoseryl-tRNA synthetase, and a codon in mRNA including said unnatural base is UADs.

7. A combination of a modified suppressor tRNA comprising an unnatural base at the first or the second position of the anticodon of a suppressor tRNA, wherein said unnatural base comprises a 2-oxo-1H-pyridine-3-yl (y) group which may have a substituted group at position 5, a 2-oxo-1H-imidazole-3-yl (z) group, a 2-formyl- 1-1H-pyrrole-1-yl (Pa) group which may have a substituted group at position 4 or a 2-nitro-1H-pyrrole-1-yl (Pn) group which may have a substituted group at position 4; and a mutant aminoacyl-tRNA synthetase which can aminoacylate the modified suppressor tRNA with a noncanonical amino acid(s), and wherein said mutant aminoacyl-tRNA synthetase is:

a mutant aminoacyl-tRNA synthetase having the amino acid sequence of SEQ ID NO: 2 in which the glutamic acid at position 418 is replaced with aspartic acid, asparagine or glutamine;

a mutant aminoacyl-tRNA synthetase having the amino acid sequence of SEQ ID NO: 2 in which the glutamic acid at position 420 is replaced with aspartic acid, asparagine, glutamine, lysine or arginine;

a mutant aminoacyl-tRNA synthetase having the amino acid sequence of SEQ ID NO: 2 in which the glutamic acid at position 418 s replaced with aspartic acid, asparagine or glutamine, and the glutamic acid at position 420 is replaced with aspartic acid, asparagine or glutamine; or a mutant aminoacyl-tRNA synthetase having the amino acid sequence of SEQ ID NO: 2 in which the glutamic acid at position 418 is replaced with asparagine, the glutamic acid at position 420 is replaced with asparagine and the threonine at position 423 is replaced with valine.

\* \* \* \* \*

SEQUENCE LISTING

```
<160> NUMBER OF SEQ ID NOS: 5

<210> SEQ ID NO 1
<211> LENGTH: 1605
<212> TYPE: DNA
<213> ORGANISM: Archaeoglobus fulgidus
<220> FEATURE:
<221> NAME/KEY: CDS
<222> LOCATION: (1)..(1605)
<223> OTHER INFORMATION:

<400> SEQUENCE: 1 atg aaa ttc gac cct cag aag tac aga gag ctt gca gag aag gac ttc      48
Met Lys Phe Asp Pro Gln Lys Tyr Arg Glu Leu Ala Glu Lys Asp Phe
1               5                   10                  15 gaa gct gca tgg aag gcc gga aag gaa att ctg gct gag aga agt ccg      96
Glu Ala Ala Trp Lys Ala Gly Lys Glu Ile Leu Ala Glu Arg Ser Pro
                20                  25                  30 aac gag ctt tat ccc aga gtg ggt ttc agc ttt ggt aag gag cac cct     144
Asn Glu Leu Tyr Pro Arg Val Gly Phe Ser Phe Gly Lys Glu His Pro
            35                  40                  45 cta ttt gcc aca att cag aga ttg agg gag gct tac ctc tcc ata gga     192
Leu Phe Ala Thr Ile Gln Arg Leu Arg Glu Ala Tyr Leu Ser Ile Gly
        50                  55                  60 ttt tct gag gtt gtg aat ccg ctg att gtt gag gat gtc cac gtt aaa     240
Phe Ser Glu Val Val Asn Pro Leu Ile Val Glu Asp Val His Val Lys
65                  70                  75                  80 aag cag ttc gga agg gag gct ttg gcc gtc ctc gac agg tgc ttc tac     288
Lys Gln Phe Gly Arg Glu Ala Leu Ala Val Leu Asp Arg Cys Phe Tyr
                85                  90                  95 ctt gcc aca ctc ccc aag ccc aat gtg ggt atc tct gcg gag aaa atc     336
Leu Ala Thr Leu Pro Lys Pro Asn Val Gly Ile Ser Ala Glu Lys Ile
            100                 105                 110 agg cag att gag gcc ata aca aag agg gag gtt gat tca aag ccc ctg     384
Arg Gln Ile Glu Ala Ile Thr Lys Arg Glu Val Asp Ser Lys Pro Leu
        115                 120                 125 cag gag att ttc cac cgc tac aag aag ggt gag att gac gga gac gat     432
Gln Glu Ile Phe His Arg Tyr Lys Lys Gly Glu Ile Asp Gly Asp Asp
```

```
                    130                 135                 140
ttg agc tac ctt att gct gaa gtt ctg gac gtt gat gac ata act gct       480
Leu Ser Tyr Leu Ile Ala Glu Val Leu Asp Val Asp Asp Ile Thr Ala
145                 150                 155                 160 gta aag ata ctc gat gaa gtc ttt cca gag ttc aag gag cta aag cca       528
Val Lys Ile Leu Asp Glu Val Phe Pro Glu Phe Lys Glu Leu Lys Pro
                    165                 170                 175 atc tcc agc acg ctc act ctc aga agc cac atg acg act ggc tgg ttc       576
Ile Ser Ser Thr Leu Thr Leu Arg Ser His Met Thr Thr Gly Trp Phe
                180                 185                 190 ata act ttg agc cac atc gcc gac aag ctc ccc cta ccc atc aaa ctc       624
Ile Thr Leu Ser His Ile Ala Asp Lys Leu Pro Leu Pro Ile Lys Leu
            195                 200                 205 ttc agc atc gac cgc tgc ttc agg agg gag cag gga gag gat gcg acg       672
Phe Ser Ile Asp Arg Cys Phe Arg Arg Glu Gln Gly Glu Asp Ala Thr
        210                 215                 220 agg ctt tac acc tac ttc tca gcc agc tgt gtt ctg gtt gat gaa gag       720
Arg Leu Tyr Thr Tyr Phe Ser Ala Ser Cys Val Leu Val Asp Glu Glu
225                 230                 235                 240 ctc agc gtt gat gac gga aag gct gtt gcc gag gct ctg cta agg cag       768
Leu Ser Val Asp Asp Gly Lys Ala Val Ala Glu Ala Leu Leu Arg Gln
                    245                 250                 255 ttc ggc ttc gag aac ttc agg ttc agg aag gac gag aag agg agc aag       816
Phe Gly Phe Glu Asn Phe Arg Phe Arg Lys Asp Glu Lys Arg Ser Lys
                260                 265                 270 tac tac atc ccc gac acg cag aca gag gta ttt gcc ttc cat ccg aag       864
Tyr Tyr Ile Pro Asp Thr Gln Thr Glu Val Phe Ala Phe His Pro Lys
            275                 280                 285 ctc gtt ggc tca agt aca aag tac agc gac ggc tgg att gag att gcc       912
Leu Val Gly Ser Ser Thr Lys Tyr Ser Asp Gly Trp Ile Glu Ile Ala
        290                 295                 300 acc ttc ggc atc tac tct ccc acg gcc ctt gcg gag tac gac att ccc       960
Thr Phe Gly Ile Tyr Ser Pro Thr Ala Leu Ala Glu Tyr Asp Ile Pro
305                 310                 315                 320 tat ccc gtg atg aat ctc ggc tta gga gtg gaa agg ctg gca atg att      1008
Tyr Pro Val Met Asn Leu Gly Leu Gly Val Glu Arg Leu Ala Met Ile
                    325                 330                 335 ctc tat ggc tac gac gat gtg agg aag atg gtt tac ccg cag att cat      1056
Leu Tyr Gly Tyr Asp Asp Val Arg Lys Met Val Tyr Pro Gln Ile His
                340                 345                 350 gga gag att aag cta agc gac ctc gac att gcg agg gaa ata aag gtt      1104
Gly Glu Ile Lys Leu Ser Asp Leu Asp Ile Ala Arg Glu Ile Lys Val
            355                 360                 365 aag gag gtc ccc cag act gct gta ggg ctg aaa att gcc cag agc att      1152
Lys Glu Val Pro Gln Thr Ala Val Gly Leu Lys Ile Ala Gln Ser Ile
        370                 375                 380 gtg gag acg gca gaa aag cac gct tcg gag ccg agc ccc tgc agc ttt      1200
Val Glu Thr Ala Glu Lys His Ala Ser Glu Pro Ser Pro Cys Ser Phe
385                 390                 395                 400 ttg gca ttt gaa ggg gag atg atg ggc aga aat gtg agg gtt tac gtg      1248
Leu Ala Phe Glu Gly Glu Met Met Gly Arg Asn Val Arg Val Tyr Val
                    405                 410                 415 gtt gag gag gag gag aac acg aag cta tgc ggt cct gct tac gcc aac      1296
Val Glu Glu Glu Glu Asn Thr Lys Leu Cys Gly Pro Ala Tyr Ala Asn
                420                 425                 430 gag gtt gtt gtt tac aaa ggg gac atc tac ggc att cca aaa acc aag      1344
Glu Val Val Val Tyr Lys Gly Asp Ile Tyr Gly Ile Pro Lys Thr Lys
            435                 440                 445 aag tgg agg agc ttc ttt gag gag ggt gtg cct acc ggc att agg tac      1392
Lys Trp Arg Ser Phe Phe Glu Glu Gly Val Pro Thr Gly Ile Arg Tyr
```

-continued

```
               450                 455                 460
atc gac ggc ttt gcc tac tat gca gca agg aag gtt gag gag gct gcg    1440
Ile Asp Gly Phe Ala Tyr Tyr Ala Ala Arg Lys Val Glu Glu Ala Ala
465                 470                 475                 480 atg agg gaa cag gag gag gtg aag gtg aaa gct agg att gta gag aac    1488
Met Arg Glu Gln Glu Glu Val Lys Val Lys Ala Arg Ile Val Glu Asn
                485                 490                 495 ctc tcg gac ata aac ctt tac atc cac gaa aac gtc agg agg tac att    1536
Leu Ser Asp Ile Asn Leu Tyr Ile His Glu Asn Val Arg Arg Tyr Ile
            500                 505                 510 ctc tgg aag aag ggg aag ata gac gtc aga gga cca ctg ttc gtt acc    1584
Leu Trp Lys Lys Gly Lys Ile Asp Val Arg Gly Pro Leu Phe Val Thr
        515                 520                 525 gtt aag gcc gaa att gag tag                                        1605
Val Lys Ala Glu Ile Glu
    530

<210> SEQ ID NO 2
<211> LENGTH: 534
<212> TYPE: PRT
<213> ORGANISM: Archaeoglobus fulgidus

<400> SEQUENCE: 2

Met Lys Phe Asp Pro Gln Lys Tyr Arg Glu Leu Ala Glu Lys Asp Phe
1               5                   10                  15

Glu Ala Ala Trp Lys Ala Gly Lys Glu Ile Leu Ala Glu Arg Ser Pro
            20                  25                  30

Asn Glu Leu Tyr Pro Arg Val Gly Phe Ser Phe Gly Lys Glu His Pro
        35                  40                  45

Leu Phe Ala Thr Ile Gln Arg Leu Arg Glu Ala Tyr Leu Ser Ile Gly
    50                  55                  60

Phe Ser Glu Val Val Asn Pro Leu Ile Val Glu Asp Val His Val Lys
65                  70                  75                  80

Lys Gln Phe Gly Arg Glu Ala Leu Ala Val Leu Asp Arg Cys Phe Tyr
                85                  90                  95

Leu Ala Thr Leu Pro Lys Pro Asn Val Gly Ile Ser Ala Glu Lys Ile
            100                 105                 110

Arg Gln Ile Glu Ala Ile Thr Lys Arg Glu Val Asp Ser Lys Pro Leu
        115                 120                 125

Gln Glu Ile Phe His Arg Tyr Lys Lys Gly Glu Ile Asp Gly Asp Asp
    130                 135                 140

Leu Ser Tyr Leu Ile Ala Glu Val Leu Asp Val Asp Asp Ile Thr Ala
145                 150                 155                 160

Val Lys Ile Leu Asp Glu Val Phe Pro Glu Phe Lys Glu Leu Lys Pro
                165                 170                 175

Ile Ser Ser Thr Leu Thr Leu Arg Ser His Met Thr Thr Gly Trp Phe
            180                 185                 190

Ile Thr Leu Ser His Ile Ala Asp Lys Leu Pro Leu Pro Ile Lys Leu
        195                 200                 205

Phe Ser Ile Asp Arg Cys Phe Arg Arg Glu Gln Gly Glu Asp Ala Thr
    210                 215                 220

Arg Leu Tyr Thr Tyr Phe Ser Ala Ser Cys Val Leu Val Asp Glu Glu
225                 230                 235                 240

Leu Ser Val Asp Asp Gly Lys Ala Val Ala Glu Ala Leu Leu Arg Gln
                245                 250                 255

Phe Gly Phe Glu Asn Phe Arg Phe Arg Lys Asp Glu Lys Arg Ser Lys
            260                 265                 270
```

```
Tyr Tyr Ile Pro Asp Thr Gln Thr Glu Val Phe Ala Phe His Pro Lys
        275                 280                 285

Leu Val Gly Ser Ser Thr Lys Tyr Ser Asp Gly Trp Ile Glu Ile Ala
        290                 295                 300

Thr Phe Gly Ile Tyr Ser Pro Thr Ala Leu Ala Glu Tyr Asp Ile Pro
305                 310                 315                 320

Tyr Pro Val Met Asn Leu Gly Leu Gly Val Glu Arg Leu Ala Met Ile
            325                 330                 335

Leu Tyr Gly Tyr Asp Val Arg Lys Met Val Tyr Pro Gln Ile His
        340                 345                 350

Gly Glu Ile Lys Leu Ser Asp Leu Asp Ile Ala Arg Glu Ile Lys Val
        355                 360                 365

Lys Glu Val Pro Gln Thr Ala Val Gly Leu Lys Ile Ala Gln Ser Ile
        370                 375                 380

Val Glu Thr Ala Glu Lys His Ala Ser Glu Pro Ser Pro Cys Ser Phe
385                 390                 395                 400

Leu Ala Phe Glu Gly Glu Met Met Gly Arg Asn Val Arg Val Tyr Val
            405                 410                 415

Val Glu Glu Glu Asn Thr Lys Leu Cys Gly Pro Ala Tyr Ala Asn
            420                 425                 430

Glu Val Val Tyr Lys Gly Asp Ile Tyr Gly Ile Pro Lys Thr Lys
            435                 440                 445

Lys Trp Arg Ser Phe Phe Glu Glu Gly Val Pro Thr Gly Ile Arg Tyr
        450                 455                 460

Ile Asp Gly Phe Ala Tyr Tyr Ala Ala Arg Lys Val Glu Glu Ala Ala
465                 470                 475                 480

Met Arg Glu Gln Glu Val Lys Val Lys Ala Arg Ile Val Glu Asn
            485                 490                 495

Leu Ser Asp Ile Asn Leu Tyr Ile His Glu Asn Val Arg Arg Tyr Ile
            500                 505                 510

Leu Trp Lys Lys Gly Lys Ile Asp Val Arg Gly Pro Leu Phe Val Thr
        515                 520                 525

Val Lys Ala Glu Ile Glu
        530

<210> SEQ ID NO 3
<211> LENGTH: 71
<212> TYPE: DNA
<213> ORGANISM: Artificial Sequence
<220> FEATURE:
<223> OTHER INFORMATION: 5'-nontemplate DNA fragment

<400> SEQUENCE: 3
gataatacga ctcactatag ccagggtggc agaggggcta tgcggcggac tctagatccg     60
ctttaccccg g                                                         71

<210> SEQ ID NO 4
<211> LENGTH: 60
<212> TYPE: DNA
<213> ORGANISM: Artificial Sequence
<220> FEATURE:
<223> OTHER INFORMATION: 5'-template DNA fragment for tRNA(PaUA)
<220> FEATURE:
<221> NAME/KEY: modified_base
<222> LOCATION: (1)..(1)
<223> OTHER INFORMATION: t is modified as 2'-O-methylthimidine
<220> FEATURE:
<221> NAME/KEY: modified_base
<222> LOCATION: (2)..(2)
```

```
<223> OTHER INFORMATION: g is modified as 2'-O-methylguanosine
<220> FEATURE:
<221> NAME/KEY: misc_feature
<222> LOCATION: (43)..(43)
<223> OTHER INFORMATION: n stands for Ds

<400> SEQUENCE: 4
tggagccagg gcccggattc gaaccggggt aaagcggatc tanagtccgc cgcatagccc    60

<210> SEQ ID NO 5
<211> LENGTH: 60
<212> TYPE: DNA
<213> ORGANISM: Artificial Sequence
<220> FEATURE:
<223> OTHER INFORMATION: 5'-template DNA fragment for tRNA(CPaA)
<220> FEATURE:
<221> NAME/KEY: modified_base
<222> LOCATION: (1)..(1)
<223> OTHER INFORMATION: t is modified as 2'-O-methylthimidine
<220> FEATURE:
<221> NAME/KEY: modified_base
<222> LOCATION: (2)..(2)
<223> OTHER INFORMATION: g is modified as 2'-O-methylguanosine
<220> FEATURE:
<221> NAME/KEY: misc_feature
<222> LOCATION: (42)..(42)
<223> OTHER INFORMATION: n stands for Ds

<400> SEQUENCE: 5
tggagccagg gcccggattc gaaccggggt aaagcggatc tngagtccgc cgcatagccc    60
```